United States Patent
Limon et al.

(10) Patent No.: US 7,794,776 B1
(45) Date of Patent: Sep. 14, 2010

(54) MODIFICATION OF POLYMER STENTS WITH RADIATION

(75) Inventors: Timothy A. Limon, Cupertino, CA (US); David C. Gale, San Jose, CA (US); Syed Faiyaz Ahmed Hossainy, Fremont, CA (US); Fuh-Wei Tang, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1082 days.

(21) Appl. No.: 11/478,974

(22) Filed: Jun. 29, 2006

(51) Int. Cl.
  *B05D 3/06* (2006.01)
  *C08F 2/46* (2006.01)
  *C08F 2/54* (2006.01)
  *C08J 7/18* (2006.01)
  *B29C 71/04* (2006.01)
  *A61F 2/06* (2006.01)

(52) U.S. Cl. .................. 427/2.1; 427/2.24; 427/2.25; 427/487; 427/496; 427/508; 427/532; 427/551; 427/553; 427/557

(58) Field of Classification Search ............ 427/2.1, 427/2.21, 2.24, 2.25, 487, 493, 496, 508, 427/532, 551, 553, 557; 623/1.11, 1.42
See application file for complete search history.

(56) References Cited

U.S. PATENT DOCUMENTS

| | | | |
|---|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |

(Continued)

FOREIGN PATENT DOCUMENTS

DE  44 07 079  9/1994

(Continued)

OTHER PUBLICATIONS

Loo et al. Radiation effects on poly (lactide-co-glycolide) and poly-l-lactide. Polymer degradation and stability. vol. 83 (2005) p. 259-265.*

(Continued)

*Primary Examiner*—Timothy H Meeks
*Assistant Examiner*—Cachet I Sellman
(74) *Attorney, Agent, or Firm*—Squire, Sanders & Dempsey L.L.P.

(57) ABSTRACT

Methods of modifying properties such as degradation rate and drug release rate of polymer stents with radiation are disclosed.

5 Claims, 5 Drawing Sheets

U.S. PATENT DOCUMENTS

| | | | |
|---|---|---|---|
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,919,893 A * | 7/1999 | Roby et al. ............... 528/310 |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |

| Patent No. | Date | Inventor |
|---|---|---|
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,131,266 A | 10/2000 | Saunders |
| 6,150,630 A | 11/2000 | Perry et al. |
| 6,153,252 A | 11/2000 | Hossainy et al. |
| 4,776,337 A | 12/2000 | Palmaz |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,521,865 B1 | 2/2003 | Jones et al. |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 7,169,178 B1 * | 1/2007 | Santos et al. ............... 623/1.42 |
| 7,175,873 B1 * | 2/2007 | Roorda et al. ............... 427/2.14 |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208259 A1 | 11/2003 | Penhasi |

| | | | |
|---|---|---|---|
| 2003/0209835 A1 | 11/2003 | Chun et al. | |
| 2003/0226833 A1 | 12/2003 | Shapovalov et al. | |
| 2003/0236565 A1 | 12/2003 | Fifer | |
| 2004/0034409 A1* | 2/2004 | Heublein et al. | 623/1.46 |
| 2004/0093077 A1 | 5/2004 | White et al. | |
| 2004/0098095 A1 | 5/2004 | Burnside et al. | |
| 2004/0111149 A1 | 6/2004 | Stinson | |
| 2004/0127970 A1 | 7/2004 | Webber | |
| 2004/0143317 A1 | 7/2004 | Stinson et al. | |
| 2004/0167610 A1 | 8/2004 | Fleming, III | |
| 2006/0034888 A1* | 2/2006 | Pacetti et al. | 424/426 |
| 2007/0254012 A1* | 11/2007 | Ludwig et al. | 424/426 |
| 2007/0299510 A1* | 12/2007 | Venkatraman et al. | 623/1.44 |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Yoshioka et al. Drug release from pol(d-l-lactide) microspheres by gamma irradiation. Journal of controller release. vol. 37 (1995) pp. 263-267.*

U.S. Appl. No. 10/317,435, filed Dec. 11, 2002, Hossainy et al.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure In polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

Nichols et al., *Electrical Insulation of Implantable Devices by Composite Polymer Coatings*, ISA Transactions, vol. 26(4), pp. 15-18 (1987).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-I-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single-chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

\* cited by examiner

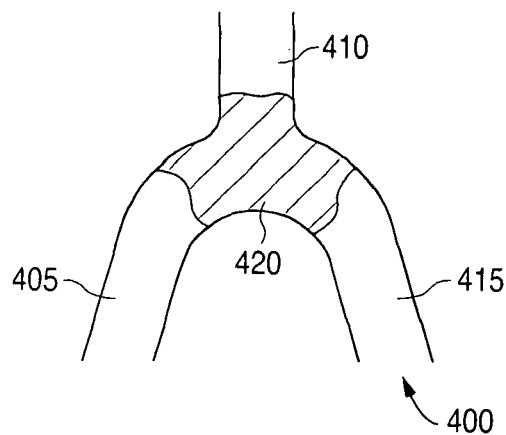
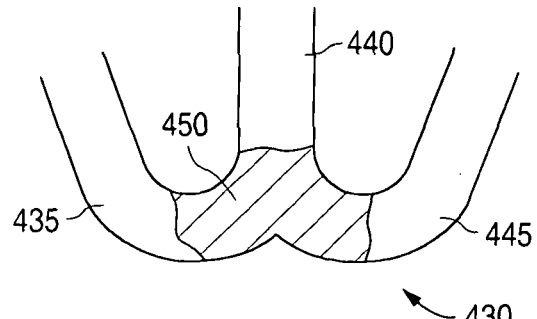
FIG. 4A          FIG. 4B
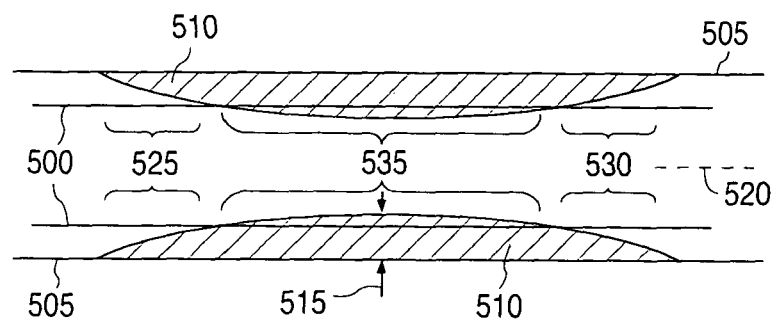
FIG. 5
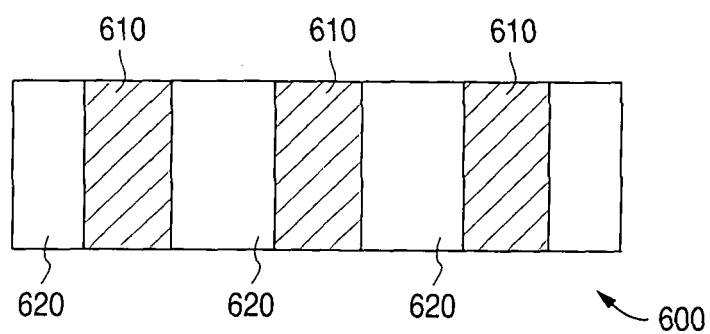
FIG. 6

MODIFICATION OF POLYMER STENTS WITH RADIATION

BACKGROUND OF THE INVENTION

1. Field of the Invention

This invention relates to methods of modifying properties of polymer stents with radiation.

Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Once expanded, the stent must adequately maintain its size and shape throughout its service life despite the various forces that may come to bear on it, including the cyclic loading induced by the beating heart. For example, a radially directed force may tend to cause a stent to recoil inward. Due to loads applied during crimping, deployment, and after deployment a stent can experience substantial stress of localized portions of the stent's structure.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

In general, it would be desirable to tailor the properties of a stent and stent coating to a desired treatment. For example, may be desirable to modify the degradation rate and drug release rate of a stent substrate or coating.

SUMMARY OF THE INVENTION

Certain embodiments of the present invention include a method of modifying a stent comprising: selecting a desired drug release rate or a degradation rate for a polymer on a stent surface; and exposing the stent to a dose of radiation capable of modifying the molecular weight of a polymer on a stent, wherein the dose modifies the molecular weight of the polymer to obtain the selected drug release rate or degradation rate.

Further embodiments of the present invention include a method of modifying a stent comprising: selecting a drug release rate or a degradation rate for a polymer of a stent; determining a range of molecular weight of the polymer to obtain the selected drug release rate or degradation rate; determining a dose of radiation exposure on the polymer sufficient so that the polymer is within the determined range of molecular weight; and exposing the coating to the determined dose of radiation.

Other embodiments of the present invention include a method of modifying a stent, comprising: selectively exposing a selected region of a surface of a stent including a polymer to a dose of radiation capable of modifying the molecular weight of the polymer, the dose of radiation modifying a drug release rate and/or a degradation of the polymer in the selected region.

Additional embodiments of the present invention include a method of modifying a stent, comprising: selectively exposing a selected region of a surface of a stent including a polymer to a dose of radiation capable of modifying the molecular weight of the polymer, the dose of radiation modifying a property of the polymer.

Further embodiments of the present invention include a method of modifying a stent, comprising: selectively directing a dose of radiation from a radiation source onto a selected region of a polymer surface of a stent, the radiation capable of modifying molecular weight of the polymer, the dose of radiation modifying properties of the polymer.

Additional embodiments of the present invention include a method of modifying a stent, comprising: disposing a mask over a surface of a stent including a polymer, the mask covering selected regions of the surface of the stent; and exposing the stent to a dose of radiation capable of modifying the molecular weight of the polymer, wherein the mask reduces or prevents exposure of the selected regions to the radiation, the radiation modifying a property of the polymer on at least a portion of the stent surface not covered by the mask.

BRIEF DESCRIPTION OF THE DRAWINGS

FIGS. 4A-B depict portions a stent with intersections of struts.

FIG. 5 depicts a schematic illustration of a stent deployed in a lumen.

FIG. 6 depicts a stent showing axial segments.

DETAILED DESCRIPTION OF THE INVENTION

The various embodiments of the present invention relate to modifying properties of a polymer stent by modifying the molecular weight or molecular weight distribution of the polymer of a stent. Embodiments of methods disclosed include modifying the molecular weight of a polymer of a stent by exposing a surface of a stent to a dose of radiation that is capable of modifying the molecular weight of the polymer. The polymer may be in a polymer substrate, scaffolding, or body of a stent. Additionally, the polymer may be in a coating disposed over a substrate, scaffolding, or body composed of metal, polymer, ceramic, or other suitable material. The polymer coating can be medicated with a drug dispersed with the polymer.

The molecular weight can be measured or characterized by molecular weight distribution(s). "Molecular weight distribution" is defined as the relative amounts of polymer chains of different molecular weights that make up a specific polymer. The number average molecular weight (Mn) is the common, mean, average of the molecular weights of the individual polymers. It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi.

Figure 1:
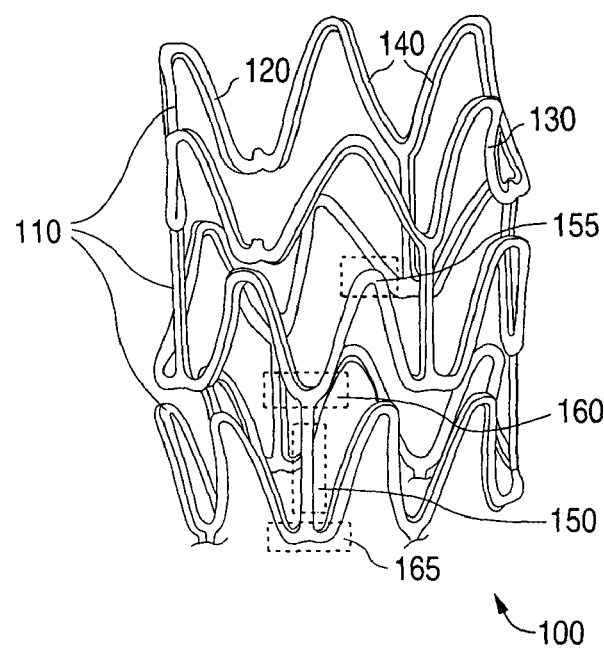
FIG. 1 depicts a stent.

The present invention can be applied to devices including, but is not limited to, self-expandable stents, balloon-expandable stents, stent-grafts, and grafts (e.g., aortic grafts). In particular, a stent can have a scaffolding or a substrate that includes a pattern of a plurality of interconnecting structural elements or struts. FIG. 1 depicts an example of a view of a stent 100. Stent 100 has a cylindrical shape that includes a pattern with a number of interconnecting structural elements or struts 110. Struts 110 of stent 100 include luminal faces or surfaces 120, abluminal faces or surfaces 130, and side-wall faces or surfaces 140. The present invention is not limited to the stent pattern depicted in FIG. 1. The variation in stent patterns is virtually unlimited.

A pattern may include portions of struts that are straight or relatively straight, an example being a portion 150. In addition, patterns may include curved portions 155, 160, and 165. Curved portions are a part of bending elements that bend inward when a stent is crimped to allow for radial compression and bend outward when a stent is expanded to allow for radial expansion. After deployment, a stent is under static and cyclic compressive loads from the vessel walls. Thus, curved portions of bending elements are subjected to stress and deformation during use. In particular, the curved portions of the bending elements are subjected to highly localized stress and deformation during use. "Use" includes, but is not limited to, manufacturing, assembling (e.g., crimping stent on a catheter), delivery of stent into and through a bodily lumen to a treatment site, and deployment of a stent at a treatment site, and treatment after deployment.

A stent such as stent 100 may be fabricated from a polymeric tube or a sheet by rolling and bonding the sheet to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers. The polymer-based coating can be a medicated layer with a drug mixed or dispersed within the polymer. Drug can be released from the coating by diffusion of the drug through and out of the coating into an implanted vessel. Alternatively or additionally, drug can be released from biodegradable coating polymer as the polymer degrades and erodes.

Several mechanisms may be relied upon for erosion and disintegration of implantable devices including, but are not limited to, mechanical, chemical breakdown and dissolution. In particular, degradation of polymers involves chemical breakdown involving enzymatic and/or hydrolytic cleavage of a device material due to exposure to bodily fluids such as blood. Hydrolysis is a chemical process in which a molecule is cleaved into two parts by the addition of a molecule of water. For example, in the degradation of polylactides, ester linkages can be broken through addition of water to form a degradation product having an acid group. Consequently, the degree of degradation in the bulk of a polymer is strongly dependent on the concentration of water in a polymer and the diffusion rate of water into the polymer.

The degradation rate may be characterized by the half-life of a polymer. The "half-life" of a degrading polymer refers to the length of time for the molecular weight of the polymer to fall to one half of its original value. See e.g., J. C. Middleton and A. J. Tipton, Biomaterials, Vol. 21 (23) (2000) pp. 2335-2346.

Degradation time refers to the time for a biodegradable coating on an implantable medical device or the time for an implantable medical device to substantially or completely erode away from an implant site. It is generally desirable for a biodegradable stent or stent coating to disintegrate and disappear once treatment is completed. For stents made from a biodegradable polymer, the stent or coating is intended to remain in the body for a duration of time until its intended function of, for example, maintaining vascular patency and/or drug delivery is accomplished. The duration of a treatment period depends on the bodily disorder that is being treated. For illustrative purposes only, the duration can be up to a month, three months, six months, twelve months, eighteen months, or two years.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind.

Figure 2:
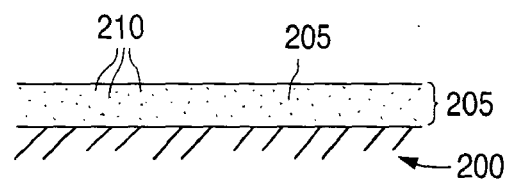
FIG. 2 depicts a cross-sectional view of a stent substrate with a coating.

FIG. 2 depicts a cross-sectional view of a stent substrate 200 with a coating that includes a polymer coating layer 205 which is a drug reservoir or medicated layer. Coating layer 205 includes a drug 210 mixed or dispersed within a polymer 215. The coating can also include a primer layer disposed between layer 205 and substrate 200. A primer layer serves as an intermediary layer for increasing the adhesion between a drug reservoir layer and surface the substrate. A coating can include any number of primer and reservoir layers. In addition, a coating can include a biobeneficial coating or topcoat layer over the reservoir layer. A biobeneficial coating can increase the biocompatibility of the coating. A topcoat layer can control the rate of drug release from a coating.

An exemplary polymer-drug coating on a polymer substrate includes a poly(DL-lactide) coating on a poly(L-lactide) substrate. An exemplary polymer-coating on a metallic substrate includes a polyester amide coating over a nitinol substrate.

As indicated above, it is desirable to tailor the properties of a substrate and stent coating. For example, the degradation rate of a polymer substrate or coating can be modified by including materials within a coating or substrate such as pore-forming agents or substances with degradation products that increase the degradation rate of the substrate or coating. Additionally, the mechanical properties of a substrate or coating can be modified by incorporating plasticizers in the coating or substrate. However, it would be desirable to modify the properties of a substrate or coating without the addition of additives.

In certain embodiments, the properties of a polymer coating or polymer substrate can be modified by exposing the polymer surface of the stent to radiation capable of modifying the molecular weight or molecular weight distribution of the polymer. In general, the properties of a polymer depend upon the molecular weight and molecular weight distribution. Properties that can be modified by modifying the molecular weight or molecular weight distribution of a polymer include, but are not limited to, degradation rate, permeability, diffusion rate of substances through the polymer, and mechanical properties such as modulus and strength. Since the degradation rate of a polymer, diffusion rate, and permeability are modified, the drug release rate from a polymer-drug coating is also modified.

Various kinds of radiation may be used to modify the molecular weight of a polymer of a stent, including, but not limited to, electron beam (e-beam), ion beam, x-ray, laser, and ultraviolet. Each of these types of radiation can cause chain scission in polymers which decreases the molecular weight. E-beam can cause chain scission with exposures at least between 5 kGy and 10 kGy. Ion beams can cause chain scission in the range of $4 \times 10^{-14}$ to $1.2 \times 10^{-14}$ ions/cm$^2$. An IR-laser is expected to cause chain scission with a pulse power of 1 W/cm$^2$ for 0.1 seconds.

For example, e-beam has been shown to cause chain scission in poly(DL-lactide) (PDLA). Specifically, e-beam radiation can cleave the labile ester bond in PDLA. A poly(L-lactide) (PLLA) tube with a PDLA coating was exposed to doses of e-beam radiation up 50 kGy. The Mn of the PDLA coating was determined at each level of exposure. A plot of e-beam radiation dose versus 1/Mn shows that the molecular weight of the PDLA coating is inversely proportional to radiation dose. Additionally, UV and x-ray radiation can also cleave the labile ester bond in PDLA. Furthermore, a laser may be used to modify the molecular weight of a polymer. The power of the laser should be high enough to cause chain scission without vaporizing the polymer. For example, an infra-read laser may be used.

The decrease in the molecular weight or Mn tends to cause an increase in the degradation rate for several reasons. Chain scission results in a larger number of smaller chain segments, many of which have acid end groups that can accelerate a hydrolysis degradation reaction. In addition, lower molecular weight polymers are closer to the final degradation products. Also, lower the molecular weight species tend to be more soluble. In addition, permeability of a polymer also increases as molecular weight decreases. As a result, there is an increase in uptake in water which increases the degradation rate through increased hydrolysis.

A decrease in molecular weight can cause an increase in drug release rate due to the increase in degradation rate and the increased permeability and diffusion of the drug through the polymer. Drug release from a stent structure can be controlled by degradation when degradation or absorption rate of the coating or substrate polymer is greater than the diffusion rate of the drug through the polymer. As a biodegradable polymer degrades or is absorbed into the body, a drug incorporated into the stent may be simultaneously released from the stent. Thus, drug release in tends to follow degradation kinetics of the polymer. It follows that drug release kinetics can be tuned or controlled by degradation rate of a coating or substrate.

Furthermore, it is well known to those of skill in the art that mechanical properties of a polymer depend on molecular weight. For example, as a polymer degrades by hydrolysis, the molecular weight decreases which is accompanied by a decrease in modulus and strength of the polymer.

Thus, radiation capable of modifying molecular weight of a polymer of a stent can be used to tailor the degradation, drug release, and mechanical properties of a polymer substrate or coating. In certain embodiments, a method of modifying a stent can include selecting a desired degradation rate, drug release rate, or value of a mechanical property for a polymer of a stent substrate or stent coating. The stent may then be exposed to a dose which can modify the molecular weight of the polymer to obtain the selected drug release rate, degradation rate, or value of mechanical property.

In some embodiments, determining the radiation dose to obtain the selected property can include determining a relationship between the molecular weight and the property. For example, the degradation rate or half-life of a polymer can be determined for various values of Mn. From the relationship of Mn and the property, an Mn range or Mn can be identified that results in the selected property, for example, a selected half-life. A radiation dose sufficient to obtain the selected property can be identified from the Mn identified and a relationship between the radiation dose and Mn.

It may be desirable to expose a polymer substrate to a different degree of radiation than a polymer coating over the substrate, since it may be desirable to modify properties of a polymer substrate to a different degree than a polymer coating. For example, it may be desirable to increase the degradation rate of the substrate to a greater degree than the coating. In some embodiments, a polymer substrate can be modified through exposure to radiation prior to applying a polymer coating. The polymer coating can then be applied and modified, if desired, through exposure to radiation, providing additional exposure and modification to the substrate.

The depth of penetration, and thus modification of the material, depends on the energy of the radiation and on the material. For example, the depth of penetration of a given material depends on the density or atomic structure. The more dense a material, the less the depth of radiation penetration will be. In general, the depth of penetration depends on the absorption of the material which can be determined from Beer's Law.

Additionally, since energy is absorbed as it passes through a material, the radiation intensity tends to decrease with penetration depth. Thus the degree of modification of the material varies with penetration depth. The radiation intensity at a given penetration depth can be increased by increasing the incident energy. Thus, one of skill in the art can modify the radiation energy to control the depth and degree of modification of a polymer material at a given depth.

Furthermore, it can be desirable to selectively modify the molecular weight, and thus, properties, of a stent with radiation. In particular, it can be useful to selectively modify the degradation rate of regions of a stent. Selective modification of degradation rate can enable control over the manner in which mechanical properties of stent degrade. Thus, the manner of failure of a stent can be controlled. In some embodiments, regions may be selectively modified to have a selected degradation rate or degradation time.

A biodegradable stent having different absorption rates on some regions may degrade and fail in a more desirable manner. As discussed above, a bioabsorbable stent is intended to remain in the body for a limited duration of time until its intended purpose has ended. Relatively small particles and/or molecules of stent material are eroded, absorbed, or resorbed due to degradation by bodily fluids and then are carried away by the bodily fluid. Degradation, erosion, absorption, and resorption of stent material result in degradation of the mechanical properties of the stent. The degradation of stent material may cause mechanical failure which may result in structural-sized portions of the stent separating from one another. The presence of such structural-sized portions may cause problems in a bodily lumen such as thrombosis and blockage. The smaller the size of such portions and the more uniform the mechanical failure of the stent, the lower the risk of such complications.

Thus, the selective modification of degradation rate can depend on the mechanical requirements of different portions. In one embodiment, regions of a stent having no or relatively no stress or strain can be selectively exposed to radiation to increase the degradation rate. As indicated above, mechanical requirements of a stent vary through the scaffolding. The curved regions of bending elements such as portions 155, 160, 165 are subjected to substantial stress ands strain during and after deployment. Straight portions, such as portion 150, experience no or relatively no stress or strain.

Figure 3:
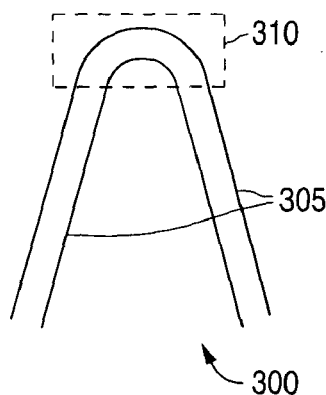
FIG. 3 depicts a portion of a stent structure having straight regions and a curved region.

FIG. 3 depicts portion 300 of a stent structure having straight regions 305 and a curved region 310. In one embodiment, straight regions 305 can be selectively exposed to a dose of radiation to increase the degradation rate, or equivalently, decrease the degradation time of straight regions 305. All or part of the straight regions may be exposed. For example, the shading depicts a region of radiation exposure. Since the mechanical requirements of straight regions 305 are lower than the curved regions 310, it can be useful to decrease their degradation time. When curved regions fail, the straight regions may be much smaller with reduced likelihood of causing problems in the lumen. The degradation rate of the straight regions can be tuned to have a selected size when the curved regions fail.

Additionally, curved regions 310 can be exposed to radiation to tune the degradation time corresponding to a selected treatment situation. In some situations, the curved regions can be modified to have a degradation rate that is faster or slower than the straight regions. In some embodiments, different regions of the stent, such as the curved regions and straight regions, can be exposed to different amounts of radiation to obtain a desired result for both the types of regions.

In some embodiments, to facilitate uniform disintegration during a selected time frame, intersections of struts can be targeted for selective exposure to radiation. For example, portions 155 and 160 include intersections of struts. FIG. 4A depicts a portion 400 of a stent with an intersection of struts 405, 410, and 415. For example, a shaded region 420 can be selectively exposed to radiation. Similarly, FIG. 4B depicts a portion 430 of a stent with an intersection of struts 435, 440, and 445. A shaded region 450 can be selectively exposed to radiation.

In additional embodiments, a stent can selectively exposed to radiation so that the degradation rate varies axially or longitudinally along a stent. For example, a stent can be exposed to radiation so that a proximal and distal end of the stent can have a different degradation rate than a middle section. In long lesions, the center portion of the lesion may be more pronounced than the ends of the lesion.

FIG. 5 depicts a schematic illustration of a stent 500 deployed in a lumen 505. Stent 500 is deployed in lumen 505 at the site of a lesion 510. A thickness 515 of lesion 510 varies along an axis 520 of lumen 505. FIG. 5 shows that lesion 510 is thickest at a center portion of the lesion and thinner at the end segments of the lesion. Therefore, the mechanical load on center portion 535 of stent 500 is greater than end segments 525 and 530. Thus, end segments 525 and 530 have a lower mechanical requirement, and thus, can be modified by radiation to have a higher degradation rate.

In other embodiments, multiple axial sections can be exposed to radiation to make the modulus and degradation rate different in the adjacent axial sections. In one embodiment, the properties of the axial section can alternate, increase or decrease along the length of the stent, or be random. FIG. 6 depicts a stent 600 having axial segments 610 and 620. Axial sections 610 have been exposed to radiation to increase the degradation rate and axial sections 620 have not been exposed or have been exposed to a different dose of radiation.

A stent having axial segments with different degradation rates and moduli can exhibit more flexibility. The increase in flexibility may be more significant when the degradation rates and moduli of the axial segments alternate. The increase in flexibility facilitates delivery of the stent through tortuous bodily lumen or implantation in an implant site that is nonlinear or that exhibits curvature. In some embodiments, as a stent degrades, the difference in mechanical properties can become more pronounced.

Various methods may be used to selectively expose regions of a stent to radiation capable of modifying molecular weight. In some embodiments, a dose of radiation can be selectively directed from a radiation source onto a selected region of a polymer surface of a stent. A system for selectively directing radiation from a radiation source onto a selected region of a stent can be adapted from a controlled deposition system that applies various substances only to certain targeted portions of an implantable medical device, such as a stent. A representative example of such a system, and a method of using the same, is described in U.S. Pat. No. 6,395,326 to Castro et al. A laser machining system for cutting stent patterns can also be adapted to selective radiation exposure of a stent. Systems for laser machining stents have been described in numerous patents including U.S. Pat. Nos. 6,521,865 and 6,131,266.

Various kinds of radiation can be selectively directed onto a stent surface including ultraviolet, ion-beam, and laser. A selective radiation system can be capable of directing radiation onto a stent surface having a complex geometry, and otherwise directing the radiation so that the treatment is limited to particular portions of the stent.

Figure 7A:
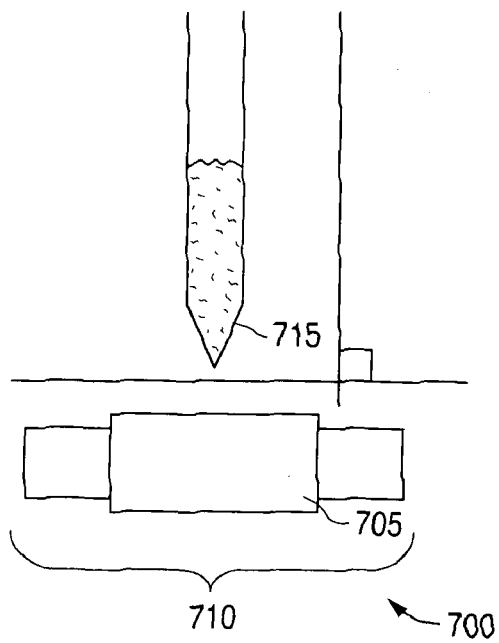
FIGS. 7A-B depict an exemplary selective irradiation systems.
Figure 7B:
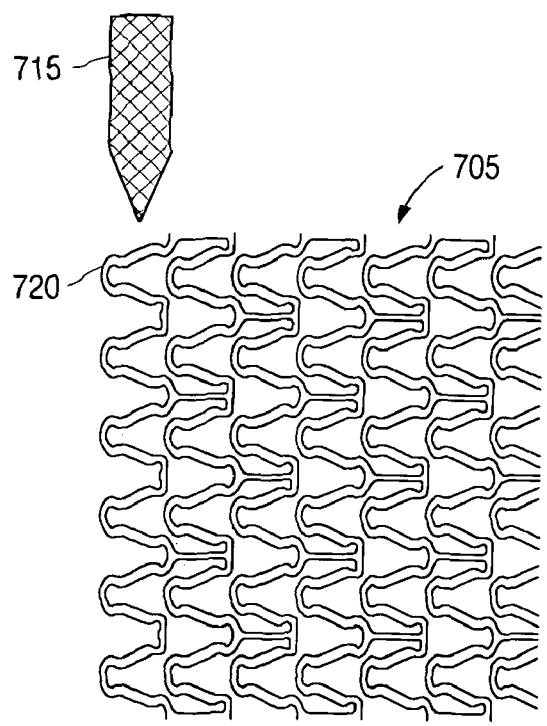

FIG. 7A depicts an exemplary selective irradiation system 700 with a stent 705 supported by a holder assembly 710 that may be coupled to a holder motion control system and a radiation source 715. FIG. 7B illustrates another view of the selective irradiation system in which radiation source 715 remains stationary during irradiation of stent 705. In this embodiment, radiation source 715 is positioned over a strut 720 of stent 705 as shown in FIG. 7B. As radiation is directed at stent 705, radiation source 715 remains stationary while stent 705 is moved via the holder motion control system along a predetermined path beneath the stationary radiation source 715, thereby causing exposure of radiation in a preselected geometrical pattern on stent 705. The predetermined path, for example, can cause exposure on stent 705 as depicted in any of the embodiments described in FIGS. 3-6. In another set of embodiments, radiation source 715 moves along a predetermined path while holder assembly 710 remains stationary during irradiation. In still another set of embodiments, both radiation source 715 and holder assembly 705 move along respective predetermined paths during irradiation.

Additional embodiments of selectively exposing regions of a stent to radiation can include masking selected regions of a stent to radiation. In some embodiments, a mask may be disposed over a polymer surface of a stent such that the mask covers selected regions of the polymer surface. The stent may then be exposed to a dose of radiation capable of modifying the molecular weight of polymer of the stent. The mask can reduce or prevent exposure of the selected regions to the radiation. The radiation can modify properties of the polymer on and beneath at least a portion of the stent surface not covered by the mask.

In some embodiments, a mask can be disposed within a stent to cover a luminal polymer surface of a stent. The inner mask can reduce or prevent exposure of regions of the inner surface due to radiation passing through gaps between stent struts. In an embodiment, an outer and inner mask can be cylindrical and be configured to fit over an abluminal surface and over an luminal surface, respectively, of a stent.

In one embodiment, the inner or luminal mask can be the same or similar to the outer mask, but having a different diameter. In other embodiments, the inner mask can be configured to cover all or a majority of an inner surface of a stent. Additional embodiments can include directing a radiation source to expose an inner surface of the stent. For example, the radiation source can directed through one or both ends of the stent. In some embodiments, the abluminal surface can be exposed to radiation and the luminal surface not exposed. Alternatively, the inner surface can be exposed and the inner surface exposed. Additionally, the abluminal surface can be exposed to a different degree of radiation than the luminal surface. Thus, the abluminal surface can have a greater or lesser degradation rate (and greater or lesser drug release rate) than the luminal surface.

The mask can be composed of any material that can shield the covered portions of the stent surface from the radiation. The mask can be composed of a polymer, metal, ceramic, or a combination thereof. Metals are generally more effective at shielding radiation such as e-beam, UV, x-ray, and ion beam. A shield that is a combination of metal and polymer and/or ceramics should have sufficient metallic content to shield the radiation.

In general, the structure of a mask can take any form that allows exposure to selected regions of a stent surface where exposure is desired to radiation directed at the stent, while reducing or preventing exposure to regions where exposure is not desired. In one embodiment, the mask can be cylindrical with at least two ring elements connected by linking or connecting elements. The structure of the mask can be configured to allow selective exposure to regions described in FIGS. 3-6.

Figure 8A:
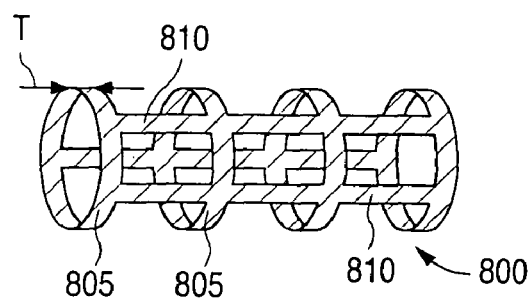
FIGS. 8A-C depict radiation masks.

FIG. 8A depicts an exemplary mask 800 that allows selective exposure of radiation to a stent surface. Mask 800 has cylindrical rings 805 connected by linking elements 810. Mask 800 can be sized to fit over or within a stent, such as stent 100 in FIG. 1. Rings 805 can be configured to cover selected regions of stent 100, such as curved regions or straight regions, when disposed over stent 100 to allow selective exposure of radiation to curved or straight regions of the stent. Cylindrical rings can have a thickness T to allow coverage of selected regions.

Figure 8B:
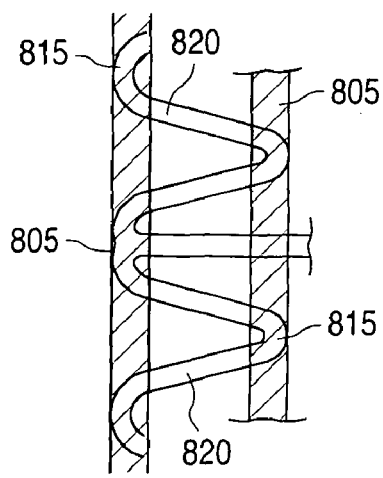
Figure 8C:
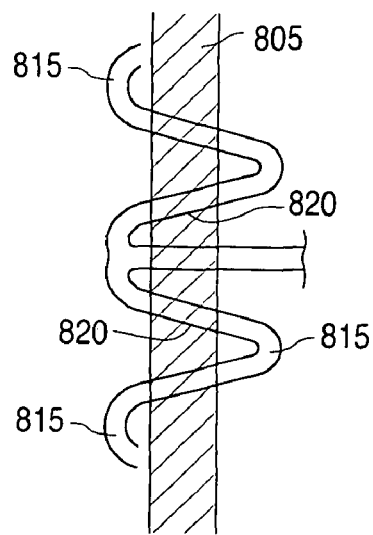

FIG. 8B depicts a portion of mask 800 disposed over an outer or abluminal surface of a stent. Rings 805 of mask 800 cover curved regions 815 and leave straight regions 820 exposed to receive a dose of radiation directed at the stent. FIG. 8C depicts a ring 805 of mask 800 also disposed over an outer or abluminal surface which covers straight regions 820 and leaves curved portions 815 exposed to receive a dose of radiation directed at the stent.

Figure 9A:
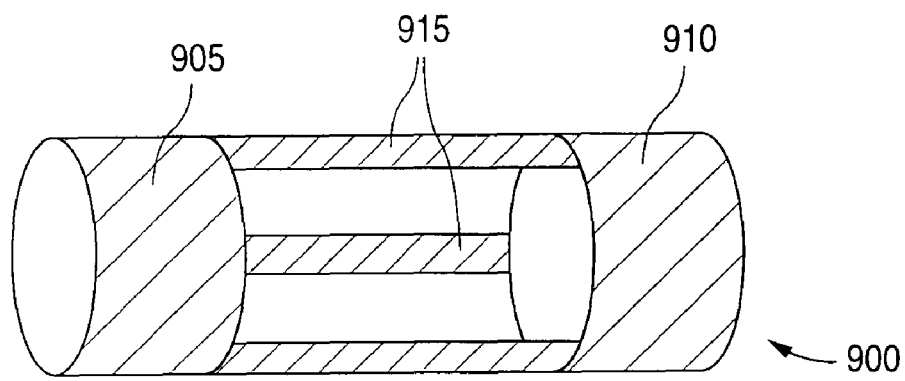
FIG. 9 depicts a radiation mask.
Figure 9B:
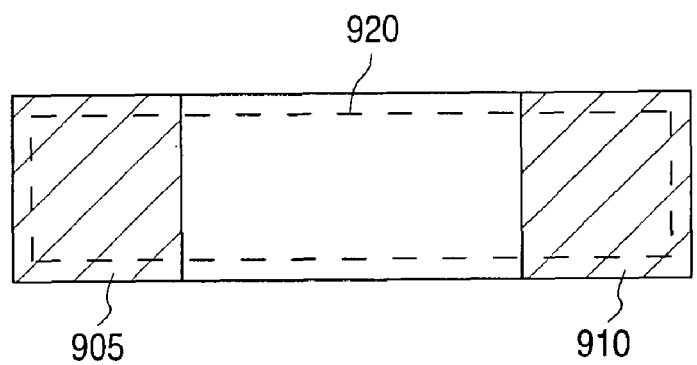

FIG. 9A depicts a mask 900 for a stent including a proximal ring 905 and a distal ring 910 for covering a proximal and a distal end of a stent, respectively. Proximal end 905 and distal end 910 are connected by linking elements 915. Alternatively, linking elements 915 can be absent and proximal ring 905 and distal ring 910 are disconnected. FIG. 9B depicts an axial cross-section of mask 900 showing rings 905 and 910 covering proximal and distal segments of a stent 920.

Figure 10:
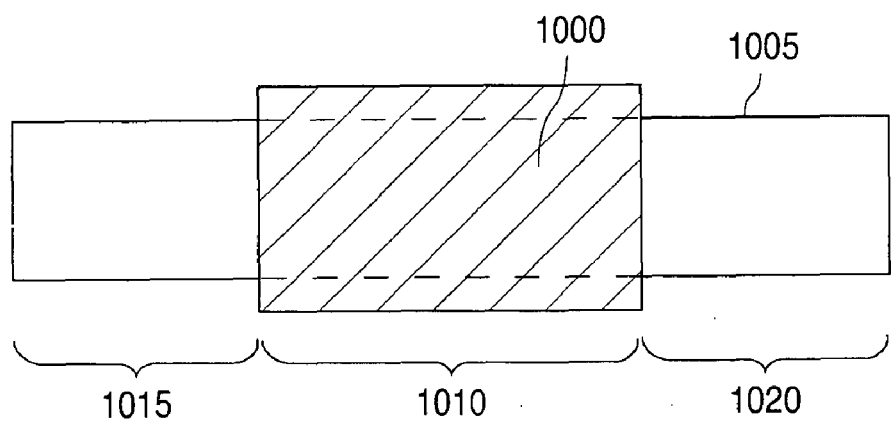
FIG. 10 depicts a radiation mask.

FIG. 10 depicts an axial cross-section of a mask 1000 that covers a central axial segment 1010 of stent 1005 to reduce or prevent exposure of radiation on segment 1010. A proximal segment 1015 and distal segment 1020 can be exposed to radiation directed at stent 1005.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene'fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

A non-polymer substrate of the stent may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Examples of drugs or active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® Capoten and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of modifying a stent comprising:
   selecting a desired drug release rate or a degradation rate for a polymer on a stent surface; and
   exposing the stent to a dose of radiation capable of modifying the molecular weight of the polymer on the stent, wherein the dose modifies the molecular weight of the polymer to obtain the selected drug release rate or degradation rate,
   wherein the polymer comprises a polyester amide coating having a drug mixed or dispersed within the coating.

2. The method of claim 1, wherein the radiation is selected from the group consisting of e-beam, ion beam, x-ray, laser, and ultraviolet.

3. A method of modifying a stent, comprising:
   selectively exposing a selected region of a surface of a stent including a polymer to a dose of radiation capable of modifying the molecular weight of the polymer, the dose of radiation modifying a property of the polymer, wherein the polymer is contained in a coating over a stent substrate, wherein the polymer is polyester amide with a drug mixed or dispersed within the coating.

4. The method of claim 3, wherein the selected region comprise curved portions or straight portions of a scaffolding of the stent.

5. The method of claim 3, wherein radiation is selected from the group consisting of e-beam, ion beam, x-ray, laser, and ultraviolet.

* * * * *